ively represent
United States Patent [19]

Sakamoto et al.

[11] Patent Number: 4,504,677
[45] Date of Patent: Mar. 12, 1985

[54] PROCESS FOR PRODUCING METHACRYLIC ACID

[75] Inventors: Teruhisa Sakamoto, Shin-nanyo; Shigeo Nakamura, Yamaguchi, both of Japan

[73] Assignee: Toyo Soda Manufacturing Co., Ltd., Shin-nanyo, Japan

[21] Appl. No.: 924,572

[22] Filed: Jul. 14, 1978

[30] Foreign Application Priority Data

Jul. 22, 1977 [JP] Japan .................. 52-87246

[51] Int. Cl.³ .................. C07C 51/25; C07C 57/055
[52] U.S. Cl. .................. 562/534; 502/170; 502/172; 502/211; 562/535; 562/536
[58] Field of Search .............. 562/535, 534; 252/435, 252/437

[56] References Cited

U.S. PATENT DOCUMENTS

| 3,761,516 | 9/1973 | Khoobiar | 562/535 |
| 3,965,163 | 6/1976 | Oda et al. | 562/535 |
| 4,000,088 | 12/1976 | Shimizu et al. | 252/437 |
| 4,001,316 | 1/1977 | Ishimi | 562/535 |
| 4,035,417 | 7/1977 | Izawa et al. | 562/535 |
| 4,072,708 | 2/1978 | White et al. | 562/535 |

Primary Examiner—Vivian Garner
Attorney, Agent, or Firm—Oblon, Fisher, Spivak, McClelland & Maier

[57] ABSTRACT

A process for producing methacrylic acid by the vapor phase catalytic oxidation of methacrolein with molecular oxygen or a molecular oxygen-containing gas comprises using a catalyst of multi-elemental complex oxide having the formula $$Mo_aP_bAs_cCu_dCr_eX_fO_g$$

wherein X represents at least one of element of Ce, Nd, W and Fe; a, b, c, d, e, f and g respectively represent atomic ratios and $a=12$, $b=0.5$ to $3.0$, $c=0.01$ to $1.2$, $d=0.01$ to $2.0$, $e=0.05$ to $2.0$ and $f=0$ to $1.0$; and g is decided on the valences of the other components such as usually 37 to 58 which is prepared with or without a reduction using a dibasic carboxylic acid, an oxycarboxylic acid, mannitol or pyrogallol.

11 Claims, No Drawings

PROCESS FOR PRODUCING METHACRYLIC ACID

BACKGROUND OF THE INVENTION

The present invention relates to a process for producing methacrylic acid by the vapor phase catalytic oxidation of methacrolein with the molecular oxygen or a molecular oxygen-containing gas. More particularly, it relates to a process for producing methacrylic acid in high yield from methacrolein by using a multi-elemental catalyst of complex oxide containing Mo, P, As, Cu, Cr and O if necessary one or more of Ce, Nd, W or Fe with or without a reducing organic agent.

Many patents and patent applications on various processes for producing unsaturated carboxylic acids such as acrylic acid or methacrylic acid by the vapor phase catalytic oxidation of the unsaturated aldehyde such as acrolein or methacrolein have been disclosed.

The process for producing acrylic acid by the oxidation of a acrolein have been practically worked in a large industrial size because of development of the catalytic systems having high catalytic activity.

However, in the process for producing methacrylic acid from methacrolein which is similar to the former, the results have been remarkably inferior to the results of the oxidation of acrolein.

The main reason is as follows. The resulting methacrylic acid is gradually oxidized to and easily decomposed into acetic acid, carbon monoxide or carbon dioxide etc. whereby a desired single flow yield of methacrylic acid (selectivity of methacrylic acid) in the industrial scale has not been obtained successfully. In general, it is not advantageous in industry and economy that the unreacted methacrolein is separated and recovered and the oxidation of methacrolein is repeated because of loss and polymerization in the recovery. Accordingly, it is important to use a catalytic system which imparts high conversion of methacrolein and high selectivity of the object methacrylic acid.

The catalytic activity (space time yield) and the catalytic durability (life) are important for the industrial operation. In the conventional processes for producing methacrylic acid, the catalytic activities are low, the reaction temperatures are remarkably high whereby remarkable decreases of the catalytic activity caused by the thermal deterioration and the desired life of the catalyst can not be obtained in the industrial operation. On the other hand, when the reaction temperature is lowered so as to prevent the decrease of the catalytic activity, a desired single flow yield of methacrylic acid can not be obtained because of low catalytic activity.

The inventors have studied to overcome these various problems and have studied various problems for developing the catalyst system which has high catalytic activity at low temperature and high selectivity and have attained the present invention.

The processes for producing methacrylic acid from methacrolein have been known. For example, it had been found that the catalysts having high catalytic properties developed for producing acrylic acid from acrolein were used for the process for oxidizing methacrolein (Mo-V-W-Cu-Cr type) in Japanese Patent Publication No. 11371/1974, etc. When these Mo-V type catalysts were used, the catalytic activity was usually too high to obtain a desired selectivity of methacrylic acid, disadvantageously.

It had been known that the Mo-P type catalysts imparting mild reactivity were used as the catalysts for oxidizing methacrolein in a vapor phase to produce methacrylic acid. With regard to the catalysts, there are many disclosures of the patent applications.

For example, in Japanese Patent Publication 19774/1972, there is the disclosure of the catalysts containing the main components of Mo and P with at least one of elements such as Cd, Tl, Pb, In, and Ge. In Japanese Patent Publication No. 24288/1950, there is the disclosure of the catalysts containing Mo, P, Tl, and at least one of elements such as Si, Al or Ti. In Japanese Unexamined Patent Publication No. 126616/1974, there is the disclosure of the catalysts containing Mo, P and V components; and in the Japanese Unexamined Patent Publication No. 96522/1975, there is the disclosure of the catalysts containing Mo, P, V, and at least one of Na, K, Rb or Cs. In USP 3,875,220, there is the disclosure of the catalysts containing the main catalysts of Mo, P and V or at least one of the elements such as Bi, As, B, Ce, Cr, Ag, Fe, W, Pb, Mn, Tl, Te, Ni, Nb, Sn and Cu.

However, when these known catalysts are used, the single flow yield of methacrylic acid is too low or the life of the catalyst or the space time yield are not satisfactory for the industrial operations.

On the other hand, in Japanese Patent Publication Nos. 10652/1974 and 3297/1975, there is the disclosure of the catalysts containing the main components of Mo and P with As.

When these catalysts are used, excellent selectivity can be obtained. However, the catalytic activity is too low and the life is not satisfactorily long. Accordingly, the catalysts containing the other metal element, or a mixture of the metal element and the alkali metal element together with said components had been known. For example, in Japanese Patent Publication No. 23014/1975, there is the disclosure of the catalysts containing Mo, P, As with at least one of V, Cu, Fe and Mn. In Japanese Unexamined Patent Publication No. 41811/1975, there is the disclosure of the catalysts containing Mo, P, As with at least one of V, W, Cu, Fe, Mn and Sn and at least one of Li, Na, K, Rb and Cs. In Japanese Unexamined Patent Publication No. 115414/1976, there is the disclosure of the catalysts containing Mo, P, As and Cu or V and at least one of Li, Na, K, Rb and Cs and at least one of Mg, Al, Si, Ca, Ti, Zr, Ag, Sb, Te, Ba and Ta. Even though some catalysts imparted relatively high single flow yield of methacrylic acid however, the catalytic activities at low temperature such as about 280° C. were unsatisfactorily low.

The inventors have studied to add various other metal components to the system of Mo, P and As. As the results, it has been surprisingly found that the multielemental complex catalysts containing Mo, P and As with both of Cu and Cr or both of Cu and Cr and at least one of Ce, Ne, W and Fe impart remarkably high catalytic activity, and moreover, when an organic compound such as dibasic carboxylic acids, oxycarboxylic acids is added for the reduction during the preparation of the catalyst, the yield is increased and the satisfactory results can be obtained in the industrial operation.

SUMMARY OF THE INVENTION

It is an object of the present invention to provide a process for producing methacrylic acid in high single flow yield or high space time yield of methacrylic acid under a long life of a catalyst.

The foregoing and other objects of the present invention have been attained by providing a process for producing methacrylic acid in high yield by the vapor phase catalytic oxidation of methacrolein with molecular oxygen or a molecular oxygen-containing gas which comprises using a catalyst of multi-elemental complex oxide having the formula $$Mo_aP_bAs_cCu_dCr_eX_fO_g$$

wherein X represents at least one of element of Ce, Nd, W and Fe; a, b, c, d, e, f and g respectively represent atomic ratios and a=12, b=0.5 to 3.0, c=0.01 to 1.2, d=0.01 to 2.0, e=0.05 to 2.0 and f=0 to 1.0; and g is decided on the valences of the other components such as usually 37 to 58, which is prepared with or without a reduction using a dibasic carboxylic acid, an oxycarboxylic acid, mannitol or pyrogallol.

DETAILED DESCRIPTION OF THE PREFERRED EMBODIMENTS

In accordance with the present invention, the catalytic activity is remarkably high and the catalyst can be used at relatively low temperature such as about 270° to 280° C., and the stable catalytic activity can be maintained for a long time whereby methacrylic acid can be produced from methacrolein in remarkably economical condition.

The catalysts of the present invention contain the important elements of Mo, P, As, Cu and Cr (and oxygen). When one of the important elements is not included in the catalyst, the single flow yield of methacrylic acid or the space time yield is too low or unsatisfactory. For example, as it is clear from the below-mentioned reference, only low single flow yield of methacrylic acid is obtained when the catalyst containing Mo, P, As and Cr or the catalyst containing Mo, P, As and Cu which does not contain either Cr or Cu, is used. However, on the contrary, high catalytic activity is attained by the catalyst containing both of Cr and Cu with Mo, P and As of the present invention. The fact is suprisingly.

The catalysts of the present invention are effective in the above-mentioned range of the components and especially impart excellent catalytic characteristics when the catalyst has the formula $$Mo_aP_bAs_cCu_dCr_eX_fO_g$$

wherein a=12, b=1.2 to 2.4, c=0.06 to 0.8, d=0.1 to 1.0, e=0.1 to 1.0, f=0 to 0.6 and g is decided on the valences of the other components such as usually 40 to 50.

Moreover, the catalytic characteristics can be further improved by the addition of an organic compound such as dibasic carboxylic acids, e.g. oxalic acid, succinic acid; oxycarboxylic acids, e.g. tartaric acid, citric acid; mannitol and pyrogallol for the reduction.

The amount of the organic compound is usually in a range of 5 to 40 wt. % preferably 10 to 20 wt. % relative to the catalytic component oxides.

The catalysts of the present invention can be prepared by the known methods, usually the precipitation-concentration method or the impregnation-supporting method, etc. The catalytic component oxide can be used as the catalyst in the present invention without supporting them on a carrier. It is possible to improve the mechanical strength of the catalyst and to easily remove the heat caused by the reaction by press-molding a mixture of the catalytic component oxide and a desired powder such as diatomaceous earth, kaolin, active clay, etc. or impregnating and supporting on a desired pre-shaped carrier such as α-alumina, silica, silica-alumina, silicon-carbide, etc. The typical method of preparing the catalyst of the present invention will be illustrated. Ammonium molybdate is used as molybdenum source. An aqueous solution of ammonium phosphate (or phosphoric acid) and ammonium arsenate is added to an aqueous solution of ammonium molybdate and then, an aqueous solution of ammonium chromate is added to the mixture, and then cuprous chloride (or cuprous bromide) is added and diatomaceous earth (or active clay) is further added to the mixture. The mixture is heated to concentrate. As the copper source, various copper compounds such as cupric nitrate, cuprous halides, cupric halides can be used. When the cuprous halide is used, superior catalytic characteristics can be obtained. In usual, cerous nitrate is used as the cerium source, neodymium nitrate is used as the neodymium source and ammonium paratungstate is used as the tungsten source and ferrous chloride or ferric nitrate is used as the iron source. When the organic compound is added, suitable amount of the organic compound is preferably added in a form of aqueous solution during the preparation of the catalyst.

In the sintering step for the catalyst of the present invention, it is unnecessary to carry out a special heat-treatment. The slurry prepared by the above-mentioned method is preferably concentrated and dried and then, it is heated to calcine it at 250° to 350° C. for several hours and further heated to sinter it at 350° to 400° C. for several to ten and several hours.

In the process of the present invention, the catalyst can be used not only in a fixed bed process but also in a fluidized bed process. The apparent contact time is usually in a range of 0.5 second to 10 seconds, preferably 1 second to 5 seconds and the pressure is preferably in a range of atmospheric pressure to 2 atm. The reaction temperature can be in a broad range of 240° to 380° C. and preferably 260° to 320° C. from the viewpoint of the space time yield and the catalytic life.

The compositions of the feed gas can be selected from the broad range. It is unnecessary to precisely limit the concentrations of methacrolein and molecular oxygen. It is preferable to select the mole ratio of the molecular oxygen to methacrolein in a range of 1 to 10, especially 1 to 5. In usual, it is preferable to feed 1 to 7 vol. % of methacrolein, 50 to 90 vol. % of air and 5 to 50 vol. % of steam. If necessary, oxygen and a diluent gas such as nitrogen, steam and carbon dioxide can be used. The starting material of methacrolein can be the product obtained by the vapor phase oxidation of isobutylene without condensing it. The starting material can contain small amount of impurities such as carbon dioxide, carbon monoxide, acetic acid, acetone or unreacted isobutylene and n-butene, butane etc.

The unreacted methacrolein can be separated and recovered and used as the starting material. The resulting methacrylic acid can be separated by the conventional methods such as a solvent-extraction method from the condensed reaction mixture.

The present invention will be illustrated by certain examples which are not construed as limiting of the invention.

The following definitions apply to the conversion of methacrolein, the selectivities of methacrylic acid, acetic acid and the single flow yield of methacrylic acid, $$\text{Conversion of methacrolein (\%)} = \frac{\text{moles of methacrolein reacted}}{\text{moles of methacrolein fed}} \times 100$$

$$\text{Selectivity (\%)} = \frac{\text{moles of each product} \times \frac{\text{carbon number of each product}}{4}}{\text{moles of methacrolein reacted}} \times 100$$

$$\text{Single flow yield of methacrylic acid (\%)} = \frac{\text{moles of methacrylic acid produced}}{\text{moles of methacrolein fed}} \times 100$$

The results of the examples and references are obtained by the following test methods.

In a Pyrex glass fixed bed reaction column having an inner diameter of 20 mm, 12 g of a catalyst was filled. The reaction column was heated in an electric tubular furnace and a feed gas containing about 5 vol. % of methacrolein, about 60 vol. % of air and 35 vol. % of steam was passed for 3 seconds of apparent contact time ($SV \approx 1,200^{hr-1}$) and the reaction temperature was in a range of 260° C. to 320° C. usually 280° C.

The catalytic life was measured by filling 40 g of a catalyst in a U shape column made of stainless steel and having an inner diameter of about 25 mm, and dipping the U shape column in a fused bath, and feeding continuously the same feed gas at the apparent constant time ($SV \approx 1,200^{hr-1}$) at the reaction temperature of 280° C. The reaction products were analyzed by the neutralization and gas chromatography.

EXAMPLE 1

In 240 ml of a distilled water heated at about 80° C., 212 g of ammonium paramolybdate $(NH_4)_6Mo_7O_{24}\cdot 4H_2O$ and 9.2 g of ammonium chromate $(NH_4)_2CrO_4$ were dissolved. The solution was admixed with 120 ml of aqueous solution containing 23.8 g of ammonium phosphate $(NH_4)_2HPO_4$ and 3.5 g of ammonium arsenate $(NH_4)_2HAsO_4$. Then, 4.0 g of cuprous chloride powder CuCl was added and 23 g of diatomaceous earth was further added to the solution. The mixture was heated and concentrated under stirring on a hot water bath.

The resulting solid product was press-molded to obtain pellets having a diameter of 5 mm and the pellets were dried at 120° C. for about 18 hours and were calcined at 300° C. for about 2 hours in air and then, were sintered at 380° C. for 6 hours to obtain the catalyst having the formula of $Mo_{12}P_{1.8}As_{0.2}Cu_{0.4}Cr_{0.6}$ (except oxygen) and containing 10 wt. % of diatomaceous earth.

The catalyst was used at the reaction temperature of 280° C. for the contact time of 3 seconds in the oxidation of methacrolein.

As the results, the conversion of methacrolein was 75.8%; the selectivity of methacrylic acid was 85.2%; the selectivity of acetic acid was 2.5%; the selectivity of carbon monoxide and carbon dioxide was 10.9% and the single flow yield of methacrylic acid was 64.6%.

Reference 1

In accordance with the process of Example 1 except adding no ammonium arsenate, a catalyst having the formula of $Mo_{12}P_{1.8}Cu_{0.4}Cr_{0.6}$ (except oxygen) and containing 10 wt. % of diatomaceous earth was prepared.

The catalyst was used in the conditions of the reaction in Example 1.

As the results, the conversion of methacrolein was 77.4%; the selectivity of methacrylic acid was 34.6%, the selectivity of acetic acid was 17.3%; and the selectivity of carbon monoxide and carbon dioxide was 47.4% and the single flow yield of methacrylic acid was 26.8%.

Reference 2

In accordance with the process of Example 1 except adding no ammonium chromate, a catalyst having the formula of $Mo_{12}P_{1.8}As_{0.2}Cu_{0.4}$ (except oxygen) and containing 10 wt. % of diatomaceous earth was prepared.

The catalyst was used in the conditions of the reaction in Example 1.

As the results, the conversion of methacrolein was 24.6%; the selectivity of methacrylic acid was 84.7%; the selectivity of acetic acid was 2.4%; the selectivity of carbon monoxide and carbon dioxide was 11.2% and the single flow yield of methacrylic acid was 20.8%.

Reference 3

In accordance with the process of Example 1 except adding no cuprous chloride, a catalyst having the formula of $Mo_{12}P_{1.8}As_{0.2}Cr_{0.6}$ (except oxygen) and containing 10 wt. % of diatomaceous earth was prepared.

The catalyst was used in the conditions of the reaction in Example 1.

As the results, the conversion of methacrolein was 21.4%; the selectivity of methacrylic acid was 83.2%; the selectivity of acetic acid was 2.9%; the selectivity of carbon monoxide and carbon dioxide was 13.7% and the single flow yield of methacrylic acid was 17.8%.

EXAMPLES 2 TO 19 AND REFERENCES 4 TO 9

In accordance with process of Example 1 except varying the amounts of the components of As, Cr, Cu and P, the catalysts having the different formula were prepared.

The catalysts were used at the reaction temperature of 280° C. for the contact time of 3 seconds in the oxidation of methacrolein.

The results are shown in Table 1.

TABLE 1

| Number | Catalytic components (atomic ratios) | | | | | Conversion of methacrolein (%) | Selectivity of methacrylic acid (%) | Single flow yield of methacrylic acid (%) |
| --- | --- | --- | --- | --- | --- | --- | --- | --- |
| | Mo | P | As | Cu | Cr | | | |
| Exp. 2 | 12 | 1.8 | 0.06 | 0.4 | 0.6 | 76.3 | 75.4 | 57.5 |
| Exp. 3 | 12 | 1.8 | 0.4 | 0.4 | 0.6 | 79.2 | 85.0 | 67.3 |
| Exp. 4 | 12 | 1.8 | 0.8 | 0.4 | 0.6 | 70.4 | 88.0 | 62.0 |
| Exp. 5 | 12 | 1.8 | 1.2 | 0.4 | 0.6 | 53.7 | 89.5 | 48.1 |
| Ref. 4 | 12 | 1.8 | 1.6 | 0.4 | 0.6 | 22.1 | 90.8 | 20.1 |
| Exp. 6 | 12 | 1.8 | 0.4 | 0.4 | 0.1 | 63.4 | 84.9 | 53.8 |

TABLE 1-continued

| Number | Catalytic components (atomic ratios) | | | | | Conversion of meth-acrolein (%) | Selectivity of methacrylic acid (%) | Single flow yield of methacrylic acid (%) |
|---|---|---|---|---|---|---|---|---|
| | Mo | P | As | Cu | Cr | | | |
| Exp. 7 | 12 | 1.8 | 0.4 | 0.4 | 0.3 | 72.9 | 87.0 | 63.4 |
| Exp. 8 | 12 | 1.8 | 0.4 | 0.4 | 0.7 | 76.6 | 86.2 | 66.0 |
| Exp. 9 | 12 | 1.8 | 0.4 | 0.4 | 1.2 | 62.7 | 85.6 | 53.7 |
| Exp. 10 | 12 | 1.8 | 0.4 | 0.4 | 2.0 | 47.4 | 85.3 | 40.4 |
| Ref. 5 | 12 | 1.8 | 0.4 | 0.4 | 3.0 | 32.5 | 84.0 | 27.3 |
| Exp. 11 | 12 | 1.8 | 0.4 | 0.06 | 0.6 | 49.7 | 83.4 | 41.4 |
| Exp. 12 | 12 | 1.8 | 0.4 | 0.2 | 0.6 | 72.3 | 86.2 | 62.3 |
| Exp. 13 | 12 | 1.8 | 0.4 | 0.8 | 0.6 | 65.8 | 87.7 | 57.8 |
| Exp. 14 | 12 | 1.8 | 0.4 | 2.0 | 0.6 | 48.7 | 86.5 | 42.1 |
| Ref. 6 | 12 | 1.8 | 0.4 | 3.0 | 0.6 | 28.0 | 86.7 | 24.3 |
| Ref. 7 | 12 | 0 | 0.4 | 0.4 | 0.6 | 37.8 | 32.7 | 12.4 |
| Ref. 8 | 12 | 0 | 1.8 | 0.4 | 0.6 | 2.7 | 94.6 | 2.6 |
| Exp. 15 | 12 | 0.5 | 0.4 | 0.4 | 0.6 | 50.2 | 80.3 | 40.3 |
| Exp. 16 | 12 | 1.2 | 0.4 | 0.4 | 0.6 | 65.0 | 82.7 | 53.8 |
| Exp. 17 | 12 | 2.0 | 0.4 | 0.4 | 0.6 | 76.7 | 85.1 | 65.3 |
| Exp. 18 | 12 | 2.4 | 0.4 | 0.4 | 0.6 | 68.4 | 86.0 | 58.8 |
| Exp. 19 | 12 | 3.0 | 0.4 | 0.4 | 0.6 | 47.5 | 86.9 | 41.3 |
| Ref. 9 | 12 | 4.0 | 0.4 | 0.4 | 0.6 | 20.6 | 89.2 | 18.4 |

EXAMPLE 20

In 200 ml of a hot water, 212 g of ammonium paramolybdate was dissolved. The solution was admixed with 100 ml of aqueous solution containing 23.8 g of ammonium phosphate and 7.0 g of ammonium arsenate. The mixture was stirred and then, 80 ml of aqueous solution containing 9.2 g of ammonium chromate was added to it. Then, 100 ml of aqueous solution containing 8.7 g of cerous nitrate $Ce(NO_3)_3.6H_2O$ and 9.6 of cupric nitrate $Cu(NO_3)_2.3H_2O$ was added to the mixture, and then 23 g of diatomaceous earth was further added to the solution. The mixture was heated and concentrated and dried under stirring. The resulting solid product was press-molded to obtain pellets having a diameter of 5 mm and the pellets were calcined at 300° C. for 2 hours and sintered at 380° C. for 6 hours to obtain the catalyst having the formula $Mo_{12}P_{1.8}As_{0.4}Cu_{0.4}Cr_{0.6}Ce_{0.2}$ (except oxygen) and containing 10 wt. % of diatomaceous earth.

The catalyst was used at the reaction temperature of 280° C. for the contact time of 3 seconds in the oxidation of methacrolein.

As the results, the conversion of methacrolein was 83.2%; the selectivity of methacrylic acid was 84.9% and the single flow yield of methacrylic acid was 70.6%.

EXAMPLES 21 TO 26 AND REFERENCES 10 TO 16

In accordance with the process of Example 20, catalysts having the components of Mo, P, As, Cu and Cr together with the component of Ce, Nd, W or Fe were prepared and catalysts having components of Mo P As Cu Cr X (X represents one or more Ce, Nd, W and Fe) from which one of the component of P, As, Cu or Cr was eliminated, were also prepared.

The catalysts were used at the reaction temperature of 280° C. for the contact time of 3 seconds in the oxidation of methacrolein.

The results are shown in Table 2.

TABLE 2

| Number | Catalytic components (atomic ratios) | | | | | | Conversion of meth-acrolein (%) | Selectivity of methacrylic acid (%) | Single flow yield of methacrylic acid (%) |
|---|---|---|---|---|---|---|---|---|---|
| | Mo | P | As | Cu | Cr | X | | | |
| Exp. 21 | 12 | 1.8 | 0.4 | 0.4 | 0.6 | $Ce_{0.4}$ | 83.7 | 85.6 | 71.6 |
| Exp. 22 | 12 | 1.8 | 0.4 | 0.4 | 0.6 | $Nd_{0.4}$ | 82.3 | 87.3 | 71.8 |
| Exp. 23 | 12 | 1.8 | 0.4 | 0.4 | 0.6 | $W_{0.6}$ | 84.0 | 85.5 | 71.8 |
| Exp. 24 | 12 | 1.8 | 0.4 | 0.4 | 0.6 | $Fe_{0.6}$ | 82.2 | 86.0 | 70.7 |
| Exp. 25 | 12 | 1.8 | 0.4 | 0.4 | 0.6 | $Ce_{0.2}Nd_{0.2}$ | 86.4 | 83.8 | 72.4 |
| Exp. 26 | 12 | 1.8 | 0.4 | 0.4 | 0.6 | $Fe_{0.2}W_{0.2}$ | 81.5 | 86.5 | 70.5 |
| Ref. 10 | 12 | 1.8 | 0.4 | 0.4 | 0 | $Ce_{0.4}$ | 37.4 | 85.7 | 32.1 |
| Ref. 11 | 12 | 1.8 | 0.4 | 0.4 | 0 | $Nd_{0.4}$ | 26.8 | 86.9 | 32.3 |
| Ref. 12 | 12 | 1.8 | 0.4 | 0.4 | 0 | $W_{0.6}$ | 29.3 | 86.1 | 25.2 |
| Ref. 13 | 12 | 1.8 | 0.4 | 0.4 | 0 | $Fe_{0.6}$ | 31.7 | 87.0 | 27.6 |
| Ref. 14 | 12 | 1.8 | 0.4 | 0 | 0.6 | $Fe_{0.6}$ | 25.5 | 82.4 | 21.0 |
| Ref. 15 | 12 | 1.8 | 0 | 0.4 | 0.6 | $W_{0.6}$ | 49.8 | 38.4 | 19.1 |
| Ref. 16 | 12 | 0 | 0.4 | 0.4 | 0.6 | $W_{0.6}$ | 36.9 | 32.3 | 11.9 |

EXAMPLE 27

In 240 ml of a distilled water heated at about 80° C. on a water bath, 212 g of ammonium paramolybdate was dissolved and then 100 ml of aqueous solution containing 23.8 g of ammonium phosphate and 7.0 g of ammonium arsenate was added to obtain a solution.

In 120 ml of water, 9.2 g of ammonium chromate was dissolved and 20 g of oxalic acid $H_2C_2O_4.2H_2O$ was added to the solution and the mixture was heated under stirring. The solution was added to the former solution under stirring, and then 4.0 g of cuprous chloride and 23 g of diatomaceous earth were added to the mixture. The resulting slurry was heated and concentrated under stirring and then, the product was press-molded to obtain pellets having a diameter of 5 mm and the pellets were dried at 160° C. for about 20 hours and was calcined at 300° C. for 3 hours and then sintered at 380° C. for 6 hours to obtain the catalyst having the formula of $Mo_{12}P_{1.8}As_{0.4}Cu_{0.4}Cr_{0.6}$ (except oxygen) and containing 10 wt. % of diatomaceous earth.

The catalyst was used at the reaction temperature of 280° C. for the contact time of 3 seconds in the oxidation of methacrolein.

As the results, the conversion of methacrolein was 87.4%; the selectivity of methacrylic acid was 86.0%; the selectivity of acetic acid was 2.3%, the selectivity of carbon monoxide and carbon dioxide was 9.8% and the single flow yield of methacrylic acid was 75.2%.

EXAMPLES 28 TO 34

In accordance with the process of Example 27 except varying the kind and amount of the organic compounds such as dibasic carboxylic acids and oxycarboxylic acids, the catalysts ($Mo_{12}P_{1.8}As_{0.4}Cu_{0.4}Cr_{0.6}$; diatomaceous earth 10 wt. %) were prepared.

The catalysts were used at the reaction temperature of 280° C. for the contact time of 3 seconds. The results are shown in Table 3.

TABLE 3

| Exp. Number | Kind of organic compound | Amount of compound | Conversion of methacrolein | Selectivity of methacrylic acid (%) | Single flow yield of methacrylic acid (%) |
|---|---|---|---|---|---|
| Exp. 28 | oxalic acid | 5 | 83.7 | 86.4 | 72.3 |
| Exp. 29 | oxalic acid | 20 | 85.3 | 87.2 | 74.4 |
| Exp. 30 | succinic acid | 10 | 86.0 | 83.8 | 72.1 |
| Exp. 31 | tartaric acid | 10 | 90.3 | 82.7 | 74.7 |
| Exp. 32 | mannitol | 10 | 79.4 | 90.2 | 71.6 |
| Exp. 33 | citric acid | 10 | 87.5 | 84.8 | 74.2 |
| Exp. 34 | pyrogallol | 10 | 88.1 | 82.3 | 72.5 |

EXAMPLE 35

In 300 ml of a distilled water heated at about 80° C. on a hot bath, 212 g of ammonium paramolybdate and 9.2 g of ammonium chromate were dissolved and 120 ml of aqueous solution containing 23.8 g of ammonium phosphate and 7.0 g of ammonium arsenate was added. Then, 80 ml of aqueous solution containing 8.7 g of cerous nitrate $Ce(NO_3)_3.6H_2O$ was added to the solution under stirring and 5.7 g of cuprous bromide was added and 20 g of oxalic acid was further added and 23 g of diatomaceous earth was added to the mixture. The mixture was heated and concentrated under stirring. The product was press-molded to obtain pellets having a diameter of 5 mm and the pellets were dried at 120° C. for 16 hours and were calcined at 300° C. for 2 hours and were sintered at 380° C. for 6 hours to obtain the catalyst having the formula $Mo_{12}P_{1.8}As_{0.4}Cu_{0.4}Cr_{0.6}Ce_{0.2}$ (except oxygen) and containing 10 wt. % of diatomaceous earth.

The catalysts were used at the reaction temperature of 280° C. for the contact time of 3 seconds in the oxidation of methacrolein.

As the results, the conversion of methacrolein was 90.2%; the selectivity of methacrylic acid was 84.7%; and the single flow yield of methacrylic acid was 76.4%.

EXAMPLE 36

In 300 ml of a distilled water heated at about 80° C. on a hot bath, 212 g of ammonium paramolybdate and 10.4 g of ammonium paratungstenate $(NH_4)_{10}W_{12}O_{41}.5H_2O$ were dissolved, and 120 ml of aqueous solution containing 23.8 g of ammonium phosphate and 7.0 g of ammonium arsenate was added to obtain the solution.

In 120 ml of water, 9.2 g of ammonium chromate was dissolved and 20 g of oxalic acid was added and the mixture was heated under stirring. The resulting solution was added to the former solution, and then, 80 ml of aqueous solution containing 8.7 g of cerous nitrate and 3.3 g of cuprous fluoride was added and 24 g of diatomaceous earth was further added to the solution. The mixture was heated and concentrated under stirring. The product was press-molded to obtain pellets having a diameter of 5 mm and the pellets were dried at 120° C. for 16 hours and were calcined at 300° C. for 3 hours in air and were sintered at 380° C. for 6 hours to obtain the catalyst having the formula of $Mo_{12}P_{1.8}As_{0.4}Cu_{0.4}Cr_{0.6}Ce_{0.2}W_{0.4}$ (except oxygen) and containing 10 wt. % of diatomaceous earth.

The catalyst was used at the reaction temperature of 280° C. for the contact time of 3 seconds in the oxidation of methacrolein.

As the results, the conversion of methacrolein was 90.3%, the selectivity of methacrylic acid was 85.5% and the single flow yield of methacrylic acid was 77.2%.

EXAMPLES 37 TO 46

In accordance with the process of Example 35 or 36 except varying the components of the Mo P As Cu Cr X type catalyst (X represents one or more of Ce, Nd, W and Fe), the catalysts were prepared.

The catalysts were used at the reaction temperature of 280° C. for the contact time of 3 seconds. The results are shown in Table 4.

TABLE 4

| Exp. No. | Catalytic components (atomic ratios) | | | | | | Conversion of methacrolein (%) | Selectivity of methacrylic acid (%) | Single flow yield of methacrylic acid (%) |
|---|---|---|---|---|---|---|---|---|---|
| | Mo | P | As | Cu | Cr | X | | | |
| Exp. 37 | 12 | 1.8 | 0.4 | 0.4 | 0.6 | $Ce_{0.4}$ | 91.4 | 84.3 | 77.1 |
| Exp. 38 | 12 | 1.8 | 0.4 | 0.4 | 0.6 | $Ce_{0.8}$ | 86.7 | 87.2 | 75.6 |
| Exp. 39 | 12 | 1.8 | 0.4 | 0.4 | 0.6 | $Nd_{0.2}$ | 88.5 | 86.1 | 76.2 |
| Exp. 40 | 12 | 1.8 | 0.4 | 0.4 | 0.6 | $Nd_{0.4}$ | 86.9 | 88.0 | 76.5 |
| Exp. 41 | 12 | 1.8 | 0.4 | 0.4 | 0.6 | $W_{0.2}$ | 86.0 | 89.4 | 76.9 |
| Exp. 42 | 12 | 1.8 | 0.4 | 0.4 | 0.6 | $W_{0.6}$ | 89.7 | 84.1 | 75.4 |
| Exp. 43 | 12 | 1.8 | 0.4 | 0.4 | 0.6 | $Fe_{0.2}$ | 84.2 | 87.6 | 73.8 |

TABLE 4-continued

| Exp. No. | Catalytic components (atomic ratios) | | | | | | Conversion of methacrolein (%) | Selectivity of methacrylic acid (%) | Single flow yield of methacrylic acid (%) |
| --- | --- | --- | --- | --- | --- | --- | --- | --- | --- |
| | Mo | P | As | Cu | Cr | X | | | |
| Exp. 44 | 12 | 1.8 | 0.4 | 0.4 | 0.6 | $Fe_{0.6}$ | 87.8 | 85.8 | 75.3 |
| Exp. 45 | 12 | 1.8 | 0.4 | 0.4 | 0.6 | $Fe_{1.2}$ | 82.6 | 87.0 | 71.9 |
| Exp. 46 | 12 | 1.8 | 0.4 | 0.4 | 0.6 | $Nd_{0.2}W_{0.4}$ | 87.5 | 86.4 | 75.6 |

EXAMPLE 47 AND REFERENCE 17

The life of the catalyst of Example 27 which had the formula of $Mo_{12}P_{1.8}As_{0.4}Cu_{0.4}Cr_{0.6}$ and contained 10 wt. % of diatomaceous earth was tested under the condition of the reaction temperature of 280° C. and SV of 1,200.

The life of the catalyst of Reference 2 which had the formula of $Mo_{12}P_{1.8}As_{0.2}Cu_{0.4}$ and contained 10 wt. % of diatomaceous earth, was also tested under the condition of the reaction temperature of 300° C. and SV of 1,200.

The results are shown in Table 5. The catalyst of Example 27 imparted remarkably high catalytic activity at low temperature and stable catalytic characteristics.

TABLE 5

| Number | Catalyst | Reaction condition | | Days for operation | Conversion of methacrolein (%) | Selectivity of methacrylic acid (%) | Single flow yield of methacrylic acid (%) |
| --- | --- | --- | --- | --- | --- | --- | --- |
| | | Reaction temp. | Bath temp. | | | | |
| Exp. 47 | $Mo_{12}P_{1.8}As_{0.4}$ | 280° C. | 267° C. | 2 | 86.7 | 85.6 | 74.2 |
| | $Cu_{0.4}Cr_{0.6}$ | " | " | 20 | 87.0 | 86.2 | 75.0 |
| | diatomaceous earth | " | 270° C. | 40 | 87.6 | 85.3 | 74.7 |
| | 10 wt.% | " | " | 60 | 87.2 | 86.1 | 75.0 |
| | | " | " | 90 | 86.0 | 86.4 | 74.3 |
| Ref. 17 | $Mo_{12}P_{1.8}As_{0.2}$ | 300° C. | 290° C. | 2 | 54.6 | 84.3 | 46.0 |
| | $Cu_{0.4}$ | " | " | 20 | 52.7 | 84.9 | 44.7 |
| | diatomaceous earth | " | 293° C. | 40 | 51.3 | 85.7 | 44.0 |
| | 10 wt. % | " | 295° C. | 60 | 48.3 | 85.0 | 41.1 |
| | | " | " | 90 | 45.1 | 84.2 | 38.0 |

What is claimed is:

1. A process for producing methacrylic acid by the vapor phase catalytic oxidation of methacrolein with molecular oxygen or a molecular oxygen-containing gas, which comprises: conducting said reaction over a catalyst of a multi-element complex oxide having the formula $$Mo_aP_bAs_cCu_dCr_eX_fO_g$$

wherein X represents at least one element selected from the group consisting of Ce, Nd, W and Fe; and a, b, c, d, e, f and g represent atomic ratios wherein a=12, b=0.5 to 3.0, c=0.01 to 1.2, d=0.01 to 2.0, e=0.05 to 2.0 and f=0 to 1.0 and g varies depending on the valences of the other components of the catalyst within the range of 37 to 58.

2. The process of claim 1, wherein said catalyst is prepared by reducing said multi-element complex oxide with a dibasic carboxylic acid, an oxycarboxylic acid, mannitol or pyrogallol.

3. The process of claim 1 or 2 wherein the elemental atomic ratios of said formula are a=12, b=1.2 to 2.4, c=0.06 to 0.8, d=0.1 to 1.0, e=0.1 to 1.0, f=0 to 0.6 and g=40 to 50.

4. The process of claim 2 wherein the amount of the dibasic carboxylic acid, oxycarboxylic acid, mannitol or pyrogallol relative to the multi-element complex oxide is in a range of 5 to 40 wt.%.

5. The process of claim 1 or 2 wherein said oxidation reaction is conducted at a temperature of 240° to 380° C.

6. The process of claim 5 wherein said temperature is 260° to 320° C.

7. The process of claim 4 or 5 wherein the contact time of the gas phase over said catalyst ranges from 0.5 to 10 seconds.

8. The process of claim 7 wherein said contact time ranges from 1 to 5 seconds.

9. The process of claim 2 or 4 wherein said dibasic carboxylic acid is oxalic acid or succinic acid and said oxycarboxylic acid is citric acid or tartaric acid.

10. The process of claim 4, wherein the amount of said organic compound ranges from 10 to 20 wt.%.

11. The process of claim 1 or 2 wherein said catalyst is supported on a carrier.

* * * * *